United States Patent
Allen et al.

(10) Patent No.: US 10,600,508 B1
(45) Date of Patent: Mar. 24, 2020

(54) TEMPORARY IDENTIFICATION SYSTEMS FOR A HEALTHCARE PROVIDER

(71) Applicant: BODYGUARD ID, LLC, Kansas City, MO (US)

(72) Inventors: Paul Allen, Kansas City, MO (US); Adam Johnson, Kansas City, MO (US); Scott Olitsky, Leawood, KS (US)

(73) Assignee: BODYGUARD ID, LLC, Kansas City, MO (US)

( * ) Notice: Subject to any disclaimer, the term of this patent is extended or adjusted under 35 U.S.C. 154(b) by 0 days.

(21) Appl. No.: 16/513,293

(22) Filed: Jul. 16, 2019

Related U.S. Application Data

(60) Provisional application No. 62/803,175, filed on Feb. 8, 2019.

(51) Int. Cl.
| | |
|---|---|
| *G16H 10/60* | (2018.01) |
| *H04N 1/23* | (2006.01) |
| *G06K 19/06* | (2006.01) |
| *G06K 7/14* | (2006.01) |
| *G06F 3/12* | (2006.01) |
| *G06Q 30/02* | (2012.01) |

(52) U.S. Cl.
CPC ........... *G16H 10/60* (2018.01); *G06F 3/1205* (2013.01); *G06F 3/1251* (2013.01); *G06K 7/1417* (2013.01); *G06K 19/06037* (2013.01); *H04N 1/2323* (2013.01); *G06Q 30/0225* (2013.01)

(58) Field of Classification Search
None
See application file for complete search history.

(56) References Cited

U.S. PATENT DOCUMENTS

| | | | |
|---|---|---|---|
| 4,730,849 A | * | 3/1988 | Siegel ................... G06K 17/00 283/70 |
| 6,685,719 B2 | | 2/2004 | Matera, Jr. |
| 8,636,708 B2 | | 1/2014 | Goolishian |
| (Continued) | | | |

FOREIGN PATENT DOCUMENTS

| | | | | |
|---|---|---|---|---|
| DE | 19804028 A1 | * | 8/1998 | ............. A61B 5/117 |
| IN | 201741018758 | | 6/2017 | |
| (Continued) | | | | |

OTHER PUBLICATIONS

Prinker, Release Your Creativity, dated 2018, http:prinker.us/?page_id=150.
(Continued)

*Primary Examiner* — Thomas D Lee
(74) *Attorney, Agent, or Firm* — Lathrop GPM LLP

(57) ABSTRACT

A method of temporarily displaying information about a patient to a healthcare provider includes: (1) providing a computing system comprising an input device and a processor in data communication with memory comprising a code generator; (2) inputting, via the input device, patient specific information into the memory for a first patient; (3) accessing the code generator to generate a first code for the first patient, the first code being based on the patient specific information; (4) providing a TCI printer having TCI, the TCI printer being in communication with the computing system; (5) placing the TCI printer on a first area of the first patient; and (6) activating the TCI printer to print the first code on the first area of the first patient.

18 Claims, 5 Drawing Sheets

(56) References Cited

U.S. PATENT DOCUMENTS

| | | |
|---|---|---|
| 9,286,615 B2 | 3/2016 | Hyde et al. |
| 9,744,254 B2 | 8/2017 | Levy |
| 2002/0114764 A1 | 8/2002 | Berryman |
| 2003/0176785 A1 | 9/2003 | Buckman et al. |
| 2003/0220822 A1 | 11/2003 | Fiala et al. |
| 2004/0208236 A1 | 10/2004 | Fenton |
| 2004/0246327 A1 | 12/2004 | Elzi |
| 2008/0287978 A1 | 11/2008 | Hickman, III |
| 2012/0107543 A1 | 5/2012 | Pickett |
| 2014/0188074 A1 | 7/2014 | Jacques et al. |
| 2015/0053759 A1 | 2/2015 | Cahill, Jr. |
| 2015/0331860 A1* | 11/2015 | Ninomiya ............ H04N 1/2187 382/306 |
| 2017/0056126 A1* | 3/2017 | Guzman ................ A61B 90/90 |
| 2017/0220747 A1 | 8/2017 | Nambiar |

FOREIGN PATENT DOCUMENTS

| | | |
|---|---|---|
| KR | 20160064616 | 6/2016 |
| WO | 2017142136 | 8/2017 |
| WO | 2017223088 | 12/2017 |

OTHER PUBLICATIONS

Smartrac, Patient Identification, dated 2018, https://www.smartrac-group.com/patient-identification.html.

* cited by examiner

US 10,600,508 B1

TEMPORARY IDENTIFICATION SYSTEMS FOR A HEALTHCARE PROVIDER

CROSS-REFERENCE TO RELATED APPLICATIONS

This application claims priority to U.S. Provisional Patent Application No. 62/803,175, filed Feb. 8, 2019, the disclosure of which is incorporated by reference herein in its entirety.

BACKGROUND

Information can be easily mixed up. While there are often opportunities to correct misinformation, in some scenarios, it is increasingly important that the correct information is presented the first time. For example, in medical settings, it is imperative that information is correctly passed from the patient to the medical staff and vice versa. Unfortunately, it is relatively common for information to be unintentionally mixed up. Improved systems and methods for ensuring that information is correctly associated with the intended target would be desirable.

SUMMARY

The following presents a simplified summary of the invention in order to provide a basic understanding of some aspects of the invention. The summary is not an extensive overview of the invention. It is not intended to identify critical element of the invention or to delineate the scope of the invention. Its sole purpose is to present some aspects of the invention in a simplified form as a prelude to the more detailed description that is presented elsewhere herein.

According to one embodiment of the invention, a method for temporarily displaying information about a patient to a healthcare provider includes first providing a computing system comprising an input device and a processor in data communication with memory comprising a code generator. Patient specific information is input into the memory for a first patient via the input device. The code generator is accessed to generate a first code for the first patient, which is based on the patient specific information for the first patient. A temporary cosmetic ink (TCI) printer having TCI is in communication with the computing system, and is placed on a first area of the first patient and activated to print the first code on the first area of the first patient. A scanner, having a scanning module, is in communication with the computing system, and is placed at the first area of the first patient, and activated to read and decode the first code of the first patient to provide a first decoded image. A display in communication with the scanning module displays the first decoded image.

According to another embodiment, a method of displaying information about a patient to a healthcare provider includes: (1) providing a computing system comprising an input device and a processor in data communication with memory comprising a code generator; (2) inputting, via the input device, patient specific information into the memory for a first patient; (3) accessing the code generator to generate a first code for the first patient, the first code being based on the patient specific information; (4) providing a TCI printer having TCI, the TCI printer being in communication with the computing system; (5) placing the TCI printer on a first area of the first patient; (6) activating the TCI printer to print the first code on the first area of the first patient; (7) providing a scanner having a scanning module and a display, the scanner being in communication with the computing system; (8) placing the scanner at the first area of the first patient; (9) activating the scanning module of the scanner to read and decode the first code of the first patient to provide a first decoded image; (10) activating the display; and (11) displaying the first decoded image on the display.

According to still another embodiment, a temporary identification system for a healthcare provider includes a TCI printer having TCI; and a computing system. The computing system has memory storing patient-specific information and a processor in data communication with the TCI printer and instructions that, when executed by the processor, performs the following steps: (a) accesses the memory; (b) retrieves at least a portion of the patient-specific information from the memory; (c) generates a code, the code being based on the patient-specific information; and (d) sends the code to the TCI printer, wherein the TCI printer prints the code on an area of a patient, the area being specific to a procedure arranged for the patient.

According to still yet another embodiment, a method of temporarily displaying information about a plurality of patients to a healthcare provider includes first providing a computing system comprising an input device, and a processor in data communication with memory comprising a code generator. Patient specific information is input, via the input device, into the memory for a first patient and a second patient. The code generator generates a first code for the first patient based on the first patient's patient specific information, and a second code for the second patient based on the second patient's patient specific information. A temporary cosmetic ink (TCI) printer having TCI is in communication with the computing system. The TCI printer is placed on a first area of the first patient and activated to print the first code on the first area of the first patient. Subsequently, the TCI printer is placed in a housing comprising a sanitizing light for a predetermined period of time. After removing the TCI printer from the housing, the TCI printer is placed on a first area of the second patient and activated to print the second code on the first area of the second patient.

DETAILED DESCRIPTION

In the medical field, it is imperative that patient specific information is associated with the correct patient. Without the correct information, it is nearly impossible for a patient to be correctly treated. While this seems common sense, prior art systems and methods of applying specific information to a patient are error prone. Ordinarily, patients in a healthcare environment receive an identification tag configured as an accessory to be worn by the patient. Often, this takes the form of a wristband. The wristband is generated by healthcare professionals when the patient checks in to the healthcare environment, and may contain information such as the patient's name, date of birth, allergies, medications, etc. Because this information is important to ensure that the patient receives suitable care, the wristbands are often made of a material (e.g., plastic) that protects the information from destruction (e.g., due to water damage, normal wear-and-tear, etc.). However, the wristbands can be uncomfortable, and patients will often remove the wristband. Without the wristband, the patient has no identification information, and therefore the healthcare professionals must rely on information that the patient provides, or information in the patient's medical records (assuming that the information is correct and up-to-date). Once the bracelet is lost, and a healthcare professional determines that it is lost, it must be replaced, often before further healthcare can be provided to the patient. The process of attaining a new wristband takes time, which can prevent the patient from receiving speedy treatment.

As medical errors, including mistreating patients because of unavailable or incorrect information, are responsible for an estimated 10% of all U.S. deaths per year, it is necessary to provide alternative identification systems that can be easily applied to the target subject, are not easily removed, and which reduce the likelihood of the spread of misinformation.

Barcodes have long been used to associate information with items, e.g., for keeping track of inventory or providing cost information to purchasers. Barcodes may also have utility in the healthcare industry for associating patient-specific information directly with a patient. According to an embodiment of the invention, prior identification accessories are replaced via a patient-specific barcode and/or patient specific human-readable information which is temporarily applied to the patient's skin. As will be described in greater detail herein, the barcode can be easily programmed and generated based on the patient's information using a computing system with a properly configured program, and nearly simultaneously be printed onto the patient in an area that is easily accessible by healthcare professionals.

Figure 1A:
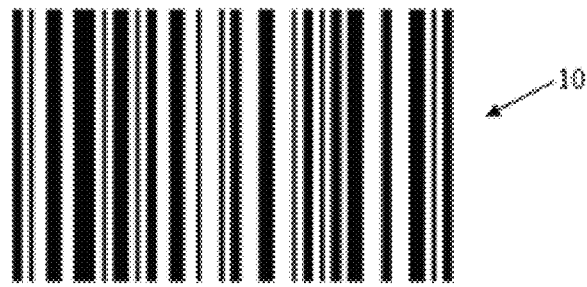
FIG. 1A illustrates a temporary identification icon according to an embodiment of the invention.
Figure 1B:
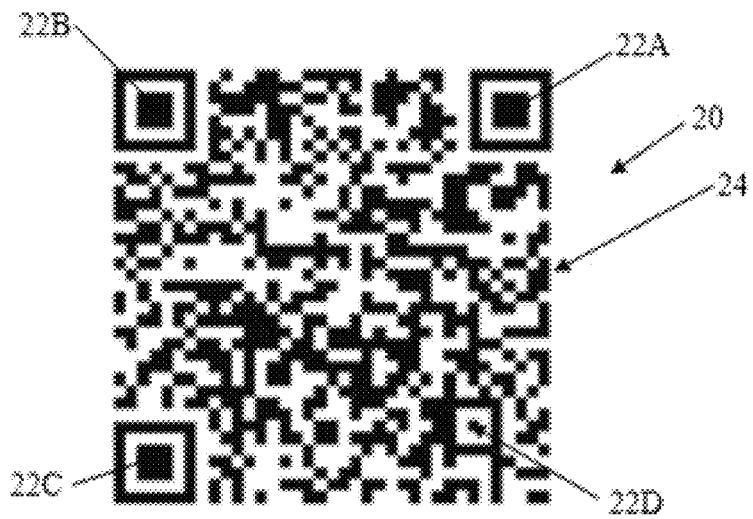
FIG. 1B illustrates a temporary identification icon according to an embodiment of the invention.

FIGS. 1A and 1B illustrates temporary identification icons (e.g., barcode) for providing specialized information according to an embodiment of the invention. The temporary identification icon may take the form of a one-dimensional barcode (FIG. 1A) having a plurality of slots. Each slot has a predefined number of stripes, including black stripes and white stripes. The slots each have the same width, and the stripes all have the same width. A unique pattern of black and white stripes is associated with each digit, from zero to nine. For example, one digit may be represented by one white stripe, two black stripes, two white stripes, and one black stripe, while another digit may be represented by one white stripe, two black stripes, one white stripe, and one final black stripe, etc. The barcode can be read and decoded by a properly configured scanner.

More preferably, the barcode may take the form of a two-dimensional barcode, such as a Quick Response (QR) code, a Datamatrix code, a PDF417 code, an Aztec code, etc. (FIG. 1B). Data is encoded in such two-dimensional barcodes in patterns, matrices, squares, hexagons, dots, and other shapes. With data encoded in both the vertical and horizontal directions, a two-dimensional barcode can store significantly more information than a similarly sized one dimensional barcode. The ability to store a large amount of information in a single QR code may be especially important in the medical field.

FIG. 1B shows a QR code 20. Each QR code includes modules that contain static information required to read the QR code 20. For example, the illustrated QR code 20 includes three edge modules 22A, 22B, and 22C (i.e., the three large squares) which identify the edges of the QR code 20 for the scanner, and an alignment marker 22D that acts as a reference point for the scanner. The QR code 20 also contains other modules and zones, such as timing pattern markers to define the positioning of the rows and columns, formatting markers to outline whether the QR code 20 contains numbers, text, symbols, or some combination thereof, a quiet zone, etc. Data and error correction information is encoded in a data encoding portion 24 of the QR code 20. As is known, QR code 20 can be read using a smart phone or any other device having an imager. To read the QR code 20, the imager of the QR code reader is used to capture an image of the QR code 20. The processor of the QR code reader then decodes the image and converts it into information meaningful to humans.

Barcodes and/or QR codes may be particularly useful in the medical field for storing patient specific information for access by medical professionals. The barcodes and/or QR codes may, in essence, be an extension of a patient's electronic medical chart which can be easily accessed merely by scanning the barcodes and/or QR codes. In embodiments, the barcodes and/or QR codes are directly associated with (e.g., printed onto) a patient's body as will be described in greater detail below.

Machine readable indicia, such as the barcode 10 and the QR code 20, can be read by computing systems quickly (as compared to Arabic numerals, for example). However, humans are typically unable to decipher such machine-readable indicia using the naked eye. To this end, machine-readable indicia may be accompanied with static information that can be readily comprehended by the naked eye. For example, the barcode 10 may include at the bottom (or elsewhere) a sequence of Arabic numerals, Greek numerals, Chinese numerals, etc. that correspond to the machine-readable indicia of the barcode 10 and allow the barcode 10 to be read both by humans and by machines. Or, for instance, where machine readable indicia on the QR code 20 translates to a patient code containing letters of the English alphabet, these letters may be listed underneath the machine-readable indicia to allow a human to comprehend the information stored in the QR code 20 with the naked eye.

Associating machine-readable indicia with static human readable indicia has several benefits. For example, if the barcode 10 or QR code 20 is deformed or is otherwise rendered unreadable by a computing system, a user may read the static human readable information provided with the barcode 10 and the QR code 20, respectively, and manually enter the information into the computing system (e.g., an electronic medical record (EMR) or other system). This may be particularly useful where the barcode 10 or the QR code 20 is updated with updated patient specific information. The static human readable information may also be used for error detection and correction, validation of the machine-readable data, security, encryption, etc. (e.g., to allow the healthcare provider to ask the patient to "confirm" the static human readable information). Thus, the barcodes and/or QR codes described herein may be provided with or without human readable indicia, and in embodiments, it may be desirable to print human readable indicia on the patient without the barcodes and/or QR codes.

Figure 2:
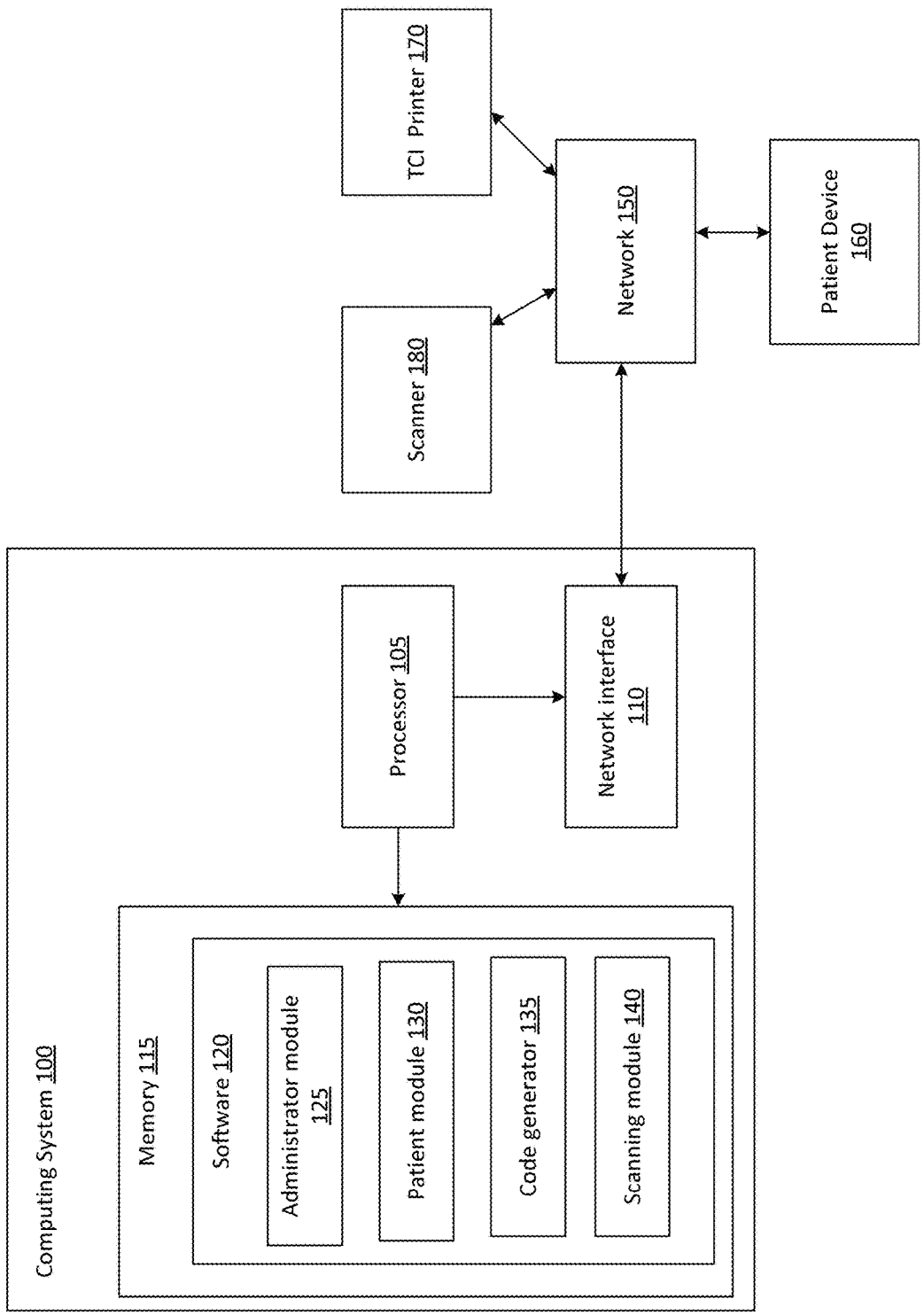
FIG. 2 is a schematic illustration of a computing system according to an embodiment of the invention.

Before the barcode 10 and/or QR code 20 can be printed on the individual, the barcode 10 and/or QR code 20 must be programmed and generated. The barcode 10 or QR code 20 (hereinafter referred to as the "code 20", which shall be understood as referring to either or both of the barcode 10 and/or the QR code 20) is generated based on patient-specific information via a computing system 100. FIG. 2 schematically illustrates an exemplary computing system configured to receive information and generate codes 20 for application to a patient via a printer as described below. The computing system 100 includes a processor 105 communicatively coupled to a network interface 110, and memory 115. The processor 105 operates software 120 housed in the memory 115. The computing system 100 may be implemented on a single device, or on several devices (e.g., devices 160, 170, and 180 in FIG. 2) that communicate over a network (e.g., network 150).

Processor 105 represents one or more digital processors. In some example embodiments, the processor 105 may be configured through particularly configured hardware, such as an application specific integrated circuit (ASIC), field-programmable gate array (FPGA), e.g., and/or through execution of software to perform functions in accordance with the disclosure herein. Network interface 110 may be implemented as one or both of a wired network interface and a wireless network interface (e.g., Wi-Fi, Internet, Bluetooth, cellular, etc.) as is known in the art. Memory 115 represents one or more of volatile memory (e.g., RAM) and non-volatile memory (e.g., ROM, EPROM, FLASH, magnetic media, optical media, etc.) Although shown within the computing system, memory 115 may be, at least in part, implemented as network storage that is external to the computing device and accessed via network interface 110.

Software 120 may be stored in a transitory or non-transitory portion of the memory 115. Software 120 includes machine-readable instructions that are executed by the processor 105 to perform the functionality of the computing system 100 as described herein. In the illustrated example, the software 120 contains one or more modes of functionality, including but not limited to a code generator 135, an administrator module 125, a patient module 130, and a scanning module 140, each of which are described in more detail below. The software 120 may contain more, or fewer, modes of functionality, depending on the needs of the healthcare provider and/or the patient. The software 120 may be located solely on the computing system 100, or may be stored on multiple devices (e.g., patient device 160, TCI printer 170, and/or scanner 180) for seamless interaction over a network 150.

The administrator module 125 may be accessed by an administrator having the appropriate credentials (e.g., login information). In the administrator module 125, the administrator may be able to access a patient's EMR (which may be stored in memory 115 or a secure database external to the computing system 100 but accessible thereby as is known in the art) for the purpose of updating and/or affirming a patient's information, such as during the patient check-in process. In one embodiment, the administrator may update the information in the patient's EMR. In another embodiment, the patient may be requested to review and approve or update the information. Once the information in the patient's EMR is updated and/or affirmed, the administrator may activate the code generator 135 to cause a code 20 to be generated based on the information in the EMR. The administrator may be required to actively enter information into the code generator 135 which should be programmed into the code 20, or the administrator may be able to select, via a selection process, the information to be included in the code 20.

As the patient may be required to review and approve or update his or her information, the software 120 may include a patient module 130. The patient module 130 may, in embodiments, communicate with a mobile computer 160 (e.g., smart phone) of a patient to allow the patient to verify his or her identity and his or her medical information, and to allow the patient to interact with the code generator 135 to customize the code 20 as discussed further below. For instance, a patient may download a mobile application, or access a website, on his or her mobile device 160 to allow him to interact with the code generator 135. The first time the patient accesses the system, the patient may be required to set up a unique profile, including defining a username and password. During subsequent logins, the user may be required to undergo a two-step authentication process, e.g., wherein a unique numerical code is sent to the patient's mobile phone 160 and used by the patient to access the system 100.

Once the patient has successfully logged into the patient module 130, the patient may first be prompted to review his or her patient records to confirm or update the records as necessary. In an embodiment, any updates by the patient via the patient module 130 may be sent to an administrator for review and/or approval prior to the information being permanently (or semi-permanently) stored in the EMR.

Once the medical information is confirmed, either by the administrator or the patient, as the case may be, the code generator 135 is activated to generate a code 20 based on the EMR. The code 20 may include general information from the patient's EMR, such as the patient's previously prescribed medications, allergies, previous surgeries, etc. Additionally, or alternately, the code 20 may be programmed to include specific information about the patient's current status, including reasons for the patient's visit to the doctor. Consider, for example, a patient that is visiting his general practitioner for an annual health screening. The code 20 may include a summary of his previous visit, a list of his previously prescribed medication(s), and a note that the patient is visiting for an annual checkup. Another patient may be visiting because of a persistent sore throat. This patient's code 20 may include a note that the patient is visiting because of a sore throat, a summary of the patient's symptoms as told to the administrator (e.g., sore throat for 3 days, no coughing, no runny nose), a list of the patient's previously prescribed medication(s), and a list of the patient's allergies. Because the code 20 is temporary and generated by the code generator 135 based on current patient information, the code 20 can be easily updated for each patient and can include only the relevant information for the health care provider for the patient's visit. This may shorten the time required by the healthcare provider to prepare for the patient's visit, and may allow the healthcare provider to begin to examine the patient, and specifically, the source of the patient's malady, much quicker than previously possible.

In still another example, the code 20 may include specific information about a patient's upcoming procedure. The patient may be admitted into a hospital for a right knee replacement. The code 20 may be programmed to include a list of the patient's date of birth, previously prescribed medication(s), a list of the patient's allergies, a note that the procedure is a right knee replacement, and the hardware required during surgery. In another example, the code 20 for a patient having open heart surgery may include the specifics of the surgery (e.g., patient is having the mitral valve replaced with a porcine mitral valve). This allows the healthcare provider to quickly review the plan for the surgery and to confirm that the correct components are available prior to the beginning of the surgery. Having reviewed the surgical plan, the doctor will be less likely to incorrectly operate on the patient, for example, by operating on an incorrect valve. Additionally, by eliminating unnecessary patient information from the code 20, the healthcare professional can quickly and easily confirm the procedure, and the location of the procedure.

As noted above, in embodiments, it may be preferable for the code 20 to include human readable indicia. Certain information, and specifically information that is imperative to the patient and the healthcare provider (such as the fact that it is a right knee replacement), may be both programmed into the code 20 itself, and may be included in a human readable message adjacent the code 20. This is to ensure that the healthcare provider(s) are acutely aware of the procedure, and the location of the procedure, to prevent mistakes.

In still other embodiments, the code 20 may be omitted, and only human readable information may be printed on the patient. Because of potential space constraints, the information may be limited to only the most necessary information. For example, for a patient undergoing a procedure, the information may include the patient's name, date of birth, type of surgery, and location of surgery.

Figure 3:
FIG. 3 is a photograph of a temporary identification icon on a patient according to an embodiment of the invention.

The patient may be permitted to interact, at least to an extent, with the code generator 135 (e.g., via the patient module 130) to customize the code 20. For example, the code generator 135 may include a database of graphics (e.g., popular characters from movies, sports graphics such as team logos, word art, etc.) accessible by the patient, as shown in FIG. 3. In embodiments, the user may upload his or her own graphics (e.g., photos) into the code generator 135, or may generate a graphic by interacting with a device such as mobile device to draw or otherwise create a graphic. The patient can scroll through the graphics and select the graphic that is most pleasing to the patient. Optionally, the patient may be permitted to select the location of the graphic relative to the code 20. When the code 20 is printed on the user, the graphic may thus be printed as well, providing a customized look for each patient. In embodiments, the patient module 130 may be limited to only allowing the patient to select a graphic, and the patient may not interact with his or her medical records.

In addition to the graphics, the patient may be able to further customize the code 20. Other customizable options may include the color of the printed code 20, the typeface of any human readable indicia, etc. In some embodiments, the patient module 130 may be altogether omitted. However, the code 20 may still be customizable, e.g., based on the patient's location, demographics, etc. For example, codes 20 generated for patients on a university campus may include a graphic related to the university. Patients in a particular age group may receive a graphic based on popular media within that age group (e.g., patients ranging in age from 3-6 may receive a graphic from a popular cartoon or recent movie). Patients in a particular location may receive a graphic based on that location (e.g., patients in Kansas City may receive a graphic based on the Kansas City Royals during baseball season, or based on the Kansas City Chiefs during football season). In certain embodiments, the code 20 may be customized with a message that is relevant to a particular time. For example, during the fall and winter, the code 20 may include a human-readable message such as "DON'T FORGET YOUR FLU SHOT. ASK ABOUT HOW YOU CAN GET ONE TODAY!" Or during an election cycle, the message may remind adults of voting age of the voting day: "EXERCISE YOUR RIGHT TO VOTE ON NOV. 4!" In still further embodiments, the code 20 may include a second area of machine-readable indicia, which may be, for example, a coupon to a favorite local spot. Thus, a child may be persuaded to allow the healthcare professional to complete the work if the child knows that he or she will receive a reward at the end, and may be excited to participate by presenting the code 20 to the staff at the local spot. Of course, those of skill in the art shall understand that there are many possibilities for customizing the code 20 and that the examples provided herein are exemplary in nature only and are not intended to be limiting.

Figure 4:
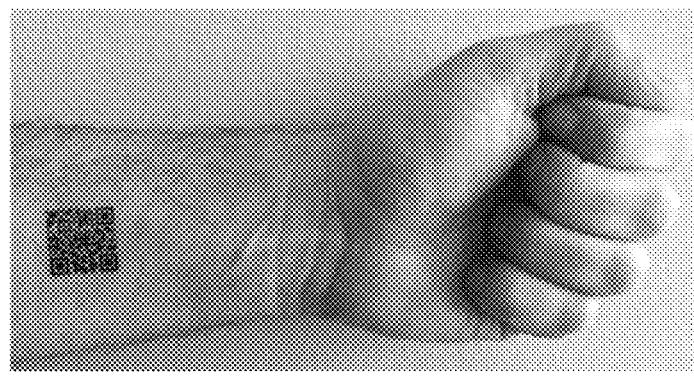
FIG. 4 is another photograph of a temporary identification icon on a patient according to another embodiment of the invention.
Figure 5:
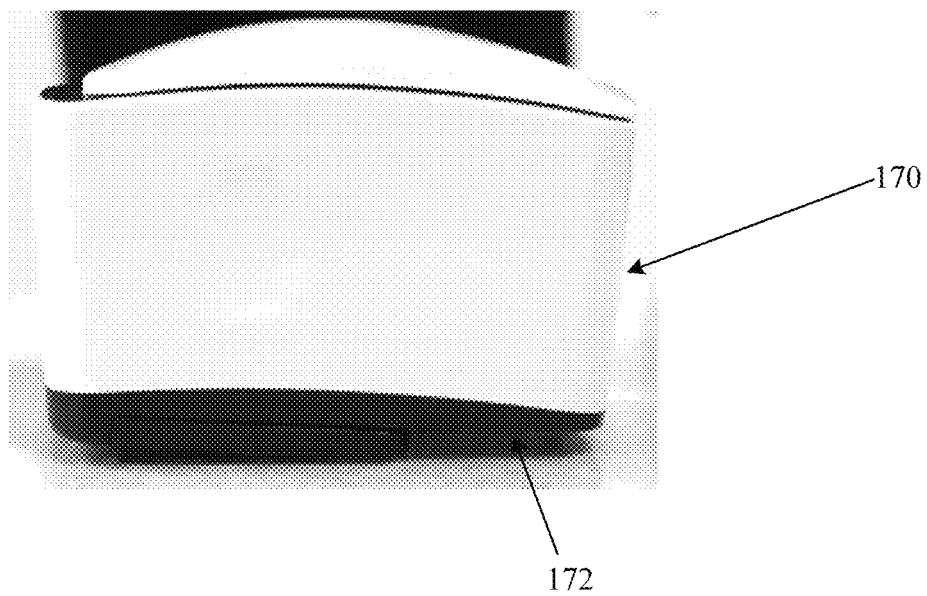
FIG. 5 is an illustration of a temporary cosmetic ink (TCI) printer according to an embodiment of the invention.

Once the code 20 is generated, a copy (e.g., digital) may be stored in the patient's EMR. The code 20 thus becomes a permanent part of the EMR providing greater protection for the patient. The code 20 may then be applied to the patient. Preferably, the code 20 is applied to the patient in an area that is easily accessible by healthcare professionals, such as on the inside of the patient's forearm or wrist, such as shown in FIG. 4. The code 20 may be applied using a temporary cosmetic ink (TCI) and a printer 170 configured to apply the TCI to the patient's body (FIG. 5). Various TCI printers 170 are known, and any TCI printer 170, whether now known or later developed, can be utilized for printing the code 20 onto the patient. One such TCI printer 170 is disclosed in U.S. Pat. No. 8,083,422. Preferably, the TCI is non-toxic and utilizes colorants that are certified by the FDA and comply with CSPC/CPSIA and ASTM requirements. In embodiments, the TCI is an alcohol-based ink that is non-toxic, water resistant, and can be washed off after several days with soap.

The TCI printer 170 is in communication (e.g., wirelessly over a network, or via a wired connection) with the computing system 100, and specifically the code generator 135, to receive the generated code from the code generator 135 for application to the patient.

The TCI printer 170 is preferably mobile and can therefore be easily transported from one location to another, and used with multiple patients. To prevent the spread of germs from one patient to the other, the TCI printer 170 may be further equipped with a sanitizing light source 172, such as an ultraviolet (e.g., UV-A, UV-B, UV-C, etc.) light for sanitizing the TCI printer 170 between patients. The UV light 172 may be selectively activated by the administrator when the TCI printer 170 is not in use. While the UV light 172 may be configured to treat the entire outer surface of the TCI printer 170, the light is at least configured to treat the surface of the TCI printer 170 that contacts the patient.

Figure 6:
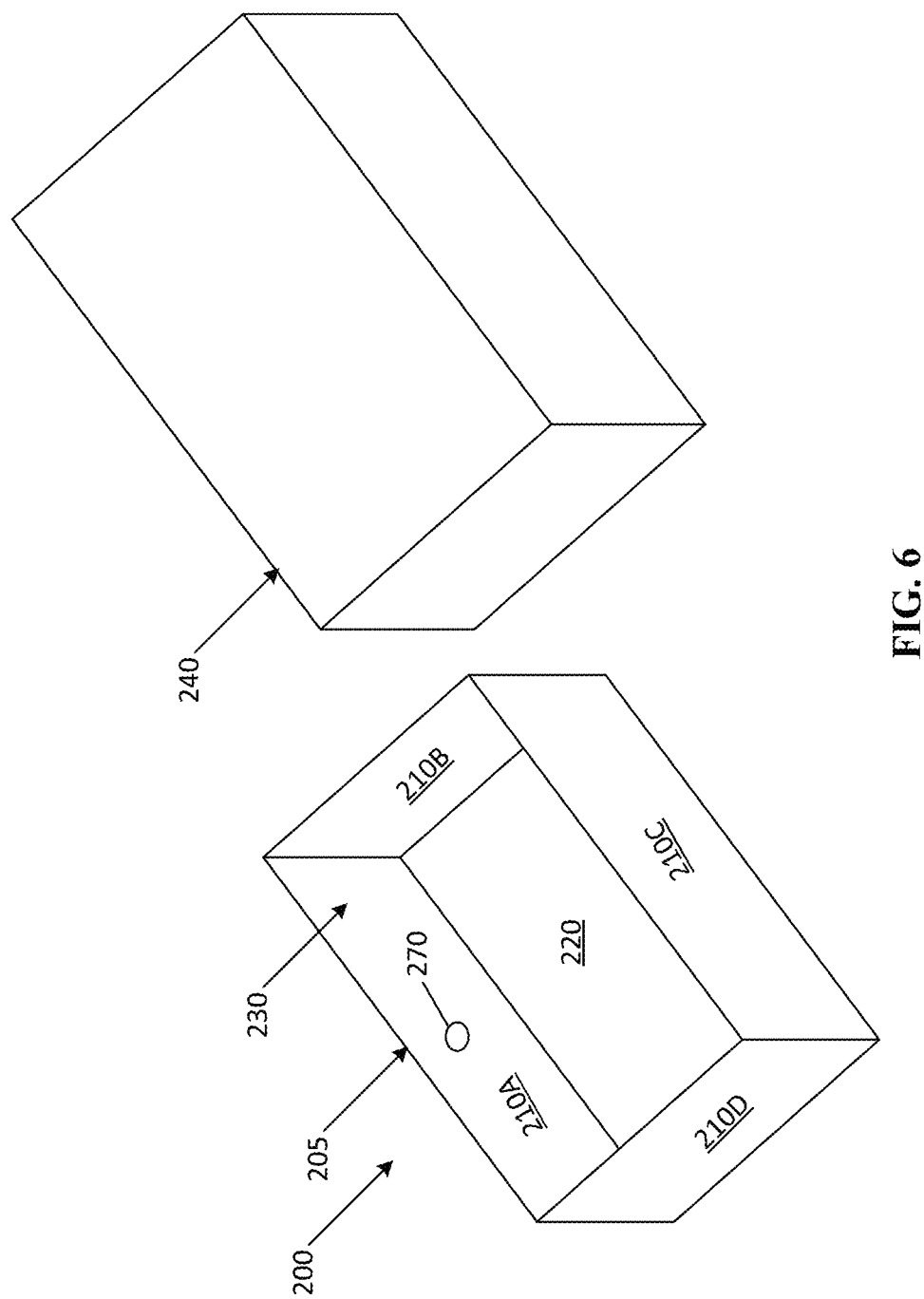
FIG. 6 is an illustration of a TCI printer housing according to an embodiment of the invention.

According to one embodiment, illustrated in FIG. 6, a housing 200 for holding the TCI printer 170 is provided. One or more UV lights 270 are disposed within the housing 200. The housing 200 generally has a main body 205 comprising four side walls 210A, 210B, 210C, and 210D and a base 220 defining an open top 230, and optionally, a cover 240 that couples to the body 205. It may be preferable for the housing 200 to be sealed, e.g., when the cover 240 is coupled to the body 205, especially where the sanitizing light source 270 may be harmful to humans. The TCI printer 170 may be situated within the housing 200, and the UV lights 270 are selectively activated to sanitize the outer surfaces of the TCI printer 170. The UV lights 270 may be manually activated via a switch, for example, or automatically activated, for example, when the cover 240 is correctly coupled to the main body 205.

The housing 200 may further include means by which the TCI printer 170 can be charged. For example, the TCI printer 170 can be battery powered, and the housing may include a charger (e.g., wired or wireless) for charging the battery.

Because the TCI printer 170 is mobile, the code 20 can be printed virtually anywhere on the patient's body. For a general visit to the doctor, the code 20 may be printed on a conspicuous, easy to reach location, such as the patient's wrist or forearm (FIG. 4). Where is patient is undergoing a procedure, the code 20 may be printed near the location of the procedure. For example, for the patient undergoing right knee replacement, the code 20 may be printed near the right knee (e.g., on the patient's lower right thigh). A patient having refractive eye surgery may have the laser settings programmed into the code 20. Having the patient-specific information printed directly on the patient, and on or near the procedure location, provides significant improvements over prior systems.

In order to read any machine-readable patient specific information programmed into the code 20, a scanner 180 is provided. The scanner 180 may be any device uniquely configured to read the code 20, including scanners that are currently available or later developed. The scanner 180 reads the code 20, and decodes the code 20 to provide the information programmed into the code 20 to the medical professional. Accordingly, in embodiments, the scanner includes an output device, or is in communication with an output device that is separate from the scanner 180. The output device may include, for example, a screen, such as a touch screen, a speaker, etc. for providing the decoded human readable information to the healthcare provider.

The scanner 180 is in communication with the computing system 100, and specifically, may be in communication with the memory 115 for storing information about the patient in the EMR. When the scanner 180 scans a code 20, scanning information may be stored in the memory 115 for later retrieval. For example, a time stamp may be stored in the patient's EMR each time the code 20 is scanned. In embodiments, each medical professional, or each team of medical professionals, may be assigned a particular identifiable scanner 180. When the scanner 180 scans the code 20, the identification of the scanner 180 and/or a time stamp can be saved into the patient's EMR.

For example, when a patient undergoes a procedure, there are often multiple teams involved. A nurse may prepare the patient for surgery, and may therefore need to verify certain patient information and/or complete certain pre-surgery measures. The nurse may therefore scan the code 20 first, and the nurse's scanner identification and time of scan may be stored in the EMR. Once the patient is prepped for surgery, an anesthesiologist may interact with the patient, and thus may scan the code 20 to ensure that the patient has no allergies and to determine the type and strength of anesthesia required for the surgery. Thus, an anesthesiologist's scanner identification and time of scan may be stored in the EMR. Finally, the surgeon may be ready to perform the surgery. To confirm the surgery, and the location of the surgery, the doctor may scan the code 20 prior to beginning, and the doctor's scanner identification and time of scan may be stored in the EMR. With the scan information stored in the EMR, the patient may be easily able to review the process of the healthcare providers in caring for the patient. Additionally, in the event of an error, it may be easy to determine whether a healthcare provider failed to access the information in the code 20, because the timestamp would not be stored in the file.

The scanner 180 may additionally include an input device. In embodiments, the input device and the output device are combined into a single device (e.g., a touchscreen). However, the input device may additionally, or alternately, include, for example, a keyboard, mouse, or other device for interacting with the scanner 180. The input device may allow the healthcare professional to further interact with a patient's EMR substantially in real time. For example, a healthcare professional can use the input device to input information into the EMR as additional information becomes available. In embodiments, the healthcare professional is provided access to the EMR by virtue of scanning the code 20, although in other embodiments, additional means of authenticating the healthcare professional's identity may be required (e.g., inputting unique login information). The ability to input information directly into the patient's EMR in real time (or substantially in real time) may aid in the timely entry of the information, and therefore improve the accuracy of the information input into the patient's EMR.

In embodiments, the TCI printer 170 also includes a scanning device. Thus, the TCI printer can both print a code 20 onto a patient, and read the code 20 once it has been applied. This may allow the printer to verify that the code 20 is properly applied and will be readable by another scanner 180. If the code 20 is not properly read by the TCI printer 170, then the TCI printer 170 can regenerate the code 20 for reapplication to the patient. In embodiments, it may be preferable to remove the defective code 20 before reapplying the new code 20. Means of removing TCI are known to those of skill in the art, and such means may be utilized to remove the defective code 20. The defective code 20 must not necessarily be removed, however, and in the event that the defective code remains, a scanner 180 may simply display an error message when reading the defective code 20, and the healthcare professional may then move to the new code for scanning.

As noted above, in embodiments, the TCI printer 170 may be in communication with the computing system 100. In certain embodiments, the TCI printer 170 is configured to scan the code 20, generate new information, or a new code 20 based on new information input into the EMR, and print the new information or new code 20 onto the patient. For example, for the patient preparing for surgery, the nurse may have recorded the patient's temperature into the EMR when prepping the patient to go into surgery. The temperature may be slightly elevated, but not concerning for the surgery, so the patient may be cleared to move to the next process, here, the anesthesiologist. The nurse may have used his or her TCI printer 170 to input the information into the EMR, or a separate input device, as the case may be. In any event, before the patient proceeds to the anesthesiologist, the nurse may rescan the code 20 using the scanning function of the TCI printer 170.

The TCI printer 170 may decode the existing code 20, and in communication with the computing device 100, determine that additional information relevant to the patient's current medical status was input into the EMR but is absent from the code 20. The TCI printer 170 may then generate an additional code 20, or an amendment to the existing code 20. The nurse may be directed (e.g., via the output device) to move the TCI printer 170 again over the old code 20, and the TCI printer 170 may then re-write the code 20 (e.g., by physically adding an additional layer of programmed code to the existing code 20, or by physically adding a separate standalone code 20) to include the additional information. For example, a version 4 QR code can support up to 50 characters. Not all characters may have been used in the initial code 20, and therefore, additional characters can be introduced to account for the new EMR information. Other versions of QR codes are known as well, and allow for more characters, and thus more information to be stored.

Moving on, once the patient has been approved for the procedure and brought to the surgical location, the anesthesiologist may scan the patient's code(s), and see that the nurse recorded a slightly elevated temperature for the patient. The anesthesiologist may thus be alerted that the patient may be exhibiting signs of illness, and that the patient's temperature should again be checked before administering the anesthetics. The anesthesiologist may record this information in the patient's EMR. If the temperature is within a normal range, the anesthesiologist may proceed, and additional details regarding the anesthesiologist's procedures with the patient may also be recorded in the EMR. If not, the patient may be returned to his room to await further instructions.

Regardless, similar to the nurse discussed above, the anesthesiologist may use his or her TCI printer 170 to decode the existing code(s) 20, and in communication with the computing system 100, determine that additional information relevant to the patient's current medical status was input into the EMR but is lacking from the code 20. The TCI printer 170 may then generate an additional code 20, or an amendment to the existing code. The anesthesiologist may be directed (e.g., via the output device) to move the TCI printer 170 again over the old code 20, and the TCI printer 170 may again re-write the code 20 (e.g., by adding an additional layer of programmed code to the existing code 20, or by adding a separate standalone code 20) to include the additional relevant information.

Assuming that the patient received the anesthetics, the patient will then proceed to the surgery. The surgeon may use a scanner 180 (or TCI printer 170) to read the code(s) 20 on the patient that now include all relevant information from the preop nurse and the anesthesiologist. The surgeon may see the information about the patient's temperature, for example, and make the final determination to postpone or proceed with the procedure. The surgeon will be able to confirm the procedure, and any information related to the procedure, before beginning.

Information may be recorded into the patient's EMR during the surgery. At the end of the surgery, similar to the nurse and anesthesiologist discussed above, the surgeon may use his or her TCI printer 170 to decode the existing code(s) 20, and in communication with the computing system 100, determine that additional information relevant to the patient's current medical status and his or her postop care was input into the EMR but is lacking from the code 20. The TCI printer 170 may then generate an additional code 20, or an amendment to the existing code 20. The surgeon may be directed (e.g., via the output device) to move the TCI printer 170 again over the old code 20, and the TCI printer 170 may again re-write the code 20 (e.g., by adding an additional layer of programmed code to the existing code 20, or by adding a separate standalone code 20) to include the additional relevant information. The postop nurse may thus have quick and easy access to the most up-to-date information about the patient that is necessary for the nurse to continue with the patient's care.

From the foregoing, it is clear that the TCI printer 170 may thus read and rewrite the code 20 that is printed on the patient. In embodiments, the TCI printer 170 may also be configured to read the human-readable indicia and supplement with additional human-readable indicia as necessary.

Additional scanners 180 may be deposited around a location for housing patients (e.g., hospitals, long-term care facilities, etc.) The scanners 180 may be able to scan the codes 20 of patients throughout the facility to track the location of the patients. Because each code 20 is unique to the patient, and directly associated with the patient, the scanner 180 can quickly identify the patient and provide an update (e.g., to a remote computing system) of the patient's location.

Without means for removing the TCI, the code 20 will remain on the patient for several days. Depending on the exposure to soap and water, the code 20 may last for a patient's entire stay, or longer. While the code 20 may be generated with certain security restrictions (e.g., a requirement that a user login to access the patient information), additional security measures may be undertaken to ensure that the codes 20 cannot be read by an unapproved scanner/user. For example, the TCI printer 170 may be configured to overprint the code 20 to obscure the code 20 from rogue scanners. As described above, the TCI printer 170 may scan the code 20 before overprinting to determine the scope of the overprint. Graphics may be printed atop the code 20, and the patient may engage with the patient module 130 as described above to customize the graphics.

While the codes 20 discussed herein are for use in the healthcare industry, codes 20 may be useful in other scenarios as well, and may be programmed with information relevant for each unique scenario. For example, codes may be utilized by persons who don't wish to carry certain personal belongings (e.g., credit cards), such as in a club, on the beach, at a concert, etc. Here, a user's credit card information can be programmed into the code 20. Here, the user may interact with a computing system (e.g., similar to computing system 100) for creating a user profile and entering his/her specific information into the user profile. Specific information from the user profile can be selectively incorporated into a code, and a code generator of the computing system may generate the code for the user. The code 20 may be printed on the user as described herein. A scanner at a point of sale (e.g., vendor on the beach, or concession area at the club or concert venue) can scan the user's code to complete a transaction rather than requiring the user to produce his or her credit card. Certain safety functionality may be programmed into the code to prevent unauthorized scanners from scanning the code, such as requiring the user to authenticate each scan prior to completing a sale. Of course, such payment functionality may also be incorporated into the codes 20 described herein, which may, for example, allow a patient to purchase items from a vending machine or store within the hospital, where permitted.

Those of skill in the art shall understand that virtually any information can be programmed into a code for printing on a user's body. According to another example, codes may be generated for members of a group, such as a classroom of kids on a field trip, a group of travelers on an excursion, patients with dementia on an outing, etc. Here, the codes for each group member may be programmed with information to contact a leader of the group, should the member get separated from the rest of the group. For example, the codes may contain the name and phone number for the group leader. The code printed on each of the group members may be identical. Optionally, a separate code may be generated for each member of the group, and may have individual-specific information, including the person's name, any medical information that may be necessary in the event of a medical emergency (e.g., mechanical heart valve, diabetic, etc.), the person's emergency contact (which may be different from the contact information of the group leader), etc.

When a group member is separated from the group, a scanner (e.g., a mobile phone equipped with a scanning app) may be used to access the information on the code, and the group leader may be contacted in order to locate the lost group member.

Many different arrangements of the various components depicted, as well as components not shown, are possible without departing from the spirit and scope of the present invention. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure. It will be understood that certain features and subcombinations are of utility and may be employed without reference to other features and subcombinations and are contemplated within the scope of the claims. The specific configurations and contours set forth in the accompanying drawings are illustrative and not limiting.

The invention claimed is:

1. A method for temporarily displaying information about a patient to a healthcare provider, comprising:
    providing a computing system comprising an input device and a processor in data communication with memory comprising a code generator;
    inputting, via the input device, patient specific information into the memory for a first patient;
    accessing the code generator to generate a first code for the first patient, the first code being based on the patient specific information for the first patient;
    providing a temporary cosmetic ink (TCI) printer having TCI, the TCI printer being in communication with the computing system;
    placing the TCI printer on a first area of the first patient;
    activating the TCI printer to print the first code on the first area of the first patient;
    providing a scanner having a scanning module, the scanner being in communication with the computing system;
    providing a display in communication with the scanning module;
    placing the scanner at the first area of the first patient;
    activating the scanning module of the scanner to read and decode the first code of the first patient to provide a first decoded image;
    activating the display;
    displaying the first decoded image on the display;
    accessing the code generator to generate a customizable indicia; and
    activating the TCI printer to print the customizable indicia on the patient.

2. The method of claim 1, wherein the first code is a machine readable QR code.

3. The method of claim 2, wherein the first code further comprises human readable indicia.

4. The method of claim 1, further comprising:
    inputting, via the input device, patient specific information into the memory for a second patient;
    accessing the code generator to generate a second code for the second patient, the second code being based on the patient specific information for the second patient;
    placing the TCI printer on a first area of the second patient;
    activating the TCI printer to print the second code on the first area of the second patient;
    placing the scanner at the first area of the second patient;
    activating the scanning module of the scanner to read and decode the second code of the second patient to provide a second decoded image;
    activating the display; and
    displaying the second decoded image on the display.

5. The method of claim 1, wherein the patient specific information comprises at least one of a procedure, a location of the procedure, and a list of hardware required for the procedure.

6. The method of claim 1, further comprising:
    storing the first code in the memory;
    inputting, via the input device, updated patient specific information into the memory for the first patient;
    accessing the first code in the memory;
    accessing the code generator to generate a second code, the second code being based on the updated patient specific information for the first patient;
    activating the TCI printer to print the second code on a second area of the first patient.

7. The method of claim 1, wherein the display is integral with the scanner.

8. The method of claim 1, wherein the customizable indicia is printed on the patient substantially contemporaneously with the first code.

9. The method of claim 1, wherein the customizable indicia is generated based on the patient specific information.

10. The method of claim 1, wherein the customizable indicia is a coupon.

11. A method for temporarily displaying information about a patient to a healthcare provider, comprising:
    providing a computing system comprising an input device and a processor in data communication with memory comprising a code generator;
    inputting, via the input device, patient specific information into the memory for a first patient;
    accessing the code generator to generate a first code for the first patient, the first code being based on the patient specific information for the first patient;
    providing a temporary cosmetic ink (TCI) printer having TCI, the TCI printer being in communication with the computing system;
    placing the TCI printer on a first area of the first patient;
    activating the TCI printer to print the first code on the first area of the first patient;
    providing a scanner having a scanning module, the scanner being in communication with the computing system;
    providing a display in communication with the scanning module;
    placing the scanner at the first area of the first patient;
    activating the scanning module of the scanner to read and decode the first code of the first patient to provide a first decoded image;
    activating the display;
    displaying the first decoded image on the display;
    storing the first code in the memory;
    inputting, via the input device, updated patient specific information into the memory for the first patient;
    accessing the first code in the memory;
    accessing the code generator to generate an update to the first code, wherein the update comprises adding machine readable indicia to the first code;
    activating the scanning module of the scanner to read the first code on the first patient; and activating the TCI printer to print the additional machine readable indicia code on the first code of the first patient.

12. The method of claim 11, wherein the scanner is integral with the TCI printer.

13. A temporary identification system for a healthcare provider, comprising:
  a temporary cosmetic ink (TCI) printer having TCI;
  a housing for the TCI printer; and
  a computing system having memory storing patient-specific information, a processor in data communication with the TCI printer, and instructions that, when executed by the processor, performs the following steps:
    (a) accesses the memory;
    (b) retrieves at least a portion of the patient-specific information from the memory;
    (c) generates a code, the code being based on the patient-specific information; and
    (d) sends the code to the TCI printer;
  wherein the TCI printer prints the code on an area of a patient, the area being specific to a procedure scheduled for the patient;
  wherein the housing comprises a sanitizing light; and
  wherein the sanitizing light is activated to sanitize the TCI printer when the TCI printer is within the housing.

14. The temporary identification system of claim 13, wherein the sanitizing light is a UV-A, UV-B, or UV-C light.

15. A method of temporarily displaying information about a plurality of patients to a healthcare provider, comprising:
  providing a computing system comprising an input device, and a processor in data communication with memory comprising a code generator;
  inputting, via the input device, patient specific information into the memory for a first patient;
  inputting, via the input device, patient specific information into the memory for a second patient;
  accessing the code generator to generate:
    a first code for the first patient, the first code being based on the patient specific information for the first patient; and
    a second code for the second patient, the second code being based on the patient specific information for the second patient;
  providing a temporary cosmetic ink (TCI) printer having TCI, the TCI printer being in communication with the computing system;
  placing the TCI printer on a first area of the first patient;
  activating the TCI printer to print the first code on the first area of the first patient;
  placing the TCI printer in a housing comprising a sanitizing light for a predetermined period of time;
  after removing the TCI printer from the housing, placing the TCI printer on a first area of the second patient; and
  activating the TCI printer to print the second code on the first area of the second patient.

16. The method of claim 15, wherein the respective first and second codes are machine-readable.

17. The method of claim 15, wherein the first code is both machine-readable and human-readable.

18. The method of claim 15, wherein the TCI printer further includes a scanner operable to read and decode the respective codes to provide respective decoded messages; and wherein the respective decoded message is communicated to the healthcare provider.

\* \* \* \* \*